United States Patent
Chen et al.

(10) Patent No.: US 9,581,014 B2
(45) Date of Patent: Feb. 28, 2017

(54) PREDICTION OF ASPHALTENE ONSET PRESSURE GRADIENTS DOWNHOLE

(71) Applicant: Schlumberger Technology Corporation, Sugar Land, TX (US)

(72) Inventors: Yi Chen, Sugar Land, TX (US);
Youxiang Zuo, Sugar Land, TX (US);
Oliver C. Mullins, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 270 days.

(21) Appl. No.: 14/164,940

(22) Filed: Jan. 27, 2014

(65) Prior Publication Data
US 2015/0211357 A1    Jul. 30, 2015

(51) Int. Cl.
*G01N 7/00* (2006.01)
*E21B 47/06* (2012.01)
*G01N 33/28* (2006.01)

(52) U.S. Cl.
CPC ......... *E21B 47/06* (2013.01); *G01N 33/2823* (2013.01)

(58) Field of Classification Search
CPC .... C10M 2207/262; C10M 2203/1025; C10N 2210/02; C10N 2230/04; C10N 2240/102; G01N 2030/3015; G01N 2030/3076; G01N 30/30; G01N 30/461; G01N 2030/025; G01N 33/2823; E21B 47/06
USPC ........................................................ 73/23.26
See application file for complete search history.

(56) References Cited

U.S. PATENT DOCUMENTS

| | | | |
|---|---|---|---|
| 7,081,615 B2 | 7/2006 | Betancourt et al. | |
| 7,822,554 B2 | 10/2010 | Zuo et al. | |
| 7,920,970 B2 | 4/2011 | Zuo et al. | |
| 7,996,154 B2 | 8/2011 | Zuo et al. | |
| 2009/0235731 A1* | 9/2009 | Zuo | G01N 33/2823 73/152.28 |
| 2009/0248310 A1* | 10/2009 | Zuo | E21B 47/102 702/11 |

(Continued)

FOREIGN PATENT DOCUMENTS

WO    2012042397 A2    4/2012

OTHER PUBLICATIONS

Zuo et al. "Integration of Fluid Log Predictions and Downhole Fluid Analysis," SPE 122562, 2009 SPE Asia Pacific Oil and Gas Conference and Exhibition, Jakarta, Indonesia, Aug. 4-6, 2009, pp. 1-11.

(Continued)

*Primary Examiner* — Eric S McCall
*Assistant Examiner* — Mohammed E Keramet-Amircolai
(74) *Attorney, Agent, or Firm* — Michael Dae

(57) ABSTRACT

A method for predicting asphaltene onset pressure in a reservoir is provided. In one embodiment, the method includes performing downhole fluid analysis of formation fluid via a downhole tool at a measurement station at a first depth in a wellbore and determining an asphaltene gradient for the formation fluid at the measurement station. Asphaltene onset pressure for a second depth in the wellbore may then be predicted based on the downhole fluid analysis and the determined asphaltene gradient. Additional methods, systems, and devices are also disclosed.

20 Claims, 6 Drawing Sheets

(56) References Cited

U.S. PATENT DOCUMENTS

| | | | |
|---|---|---|---|
| 2009/0312997 A1* | 12/2009 | Freed | E21B 49/00 703/10 |
| 2010/0062957 A1* | 3/2010 | Bertram | C10M 159/22 508/460 |
| 2011/0088949 A1 | 4/2011 | Zuo et al. | |
| 2012/0296617 A1 | 11/2012 | Zuo et al. | |
| 2013/0112406 A1* | 5/2013 | Zuo | E21B 49/10 166/250.08 |
| 2013/0151159 A1* | 6/2013 | Pomerantz | E21B 49/082 702/11 |
| 2013/0197808 A1* | 8/2013 | Zuo | E21B 47/00 702/6 |
| 2014/0137827 A1* | 5/2014 | Garner | C10M 139/00 123/1 A |
| 2014/0200810 A1* | 7/2014 | Zuo | E21B 49/10 702/13 |
| 2015/0247942 A1* | 9/2015 | Pomerantz | G01V 1/40 702/11 |

OTHER PUBLICATIONS

Zuo et al. "Investigation of Formation Connectivity Using Asphaltene Gradient Log Predictions Coupled with Downhole Fluid Analysis," SPE 124264, 2009 SPE Annual Technical Conference and Exhibition, New Orleans, Louisiana, USA, Oct. 4-7, 2009, pp. 1-11.

Alboudwarej et al. "Regular Solution Model for Asphaltene Precipitation from Bitumens and Solvents", AIChE Journal, vol. 49, No. 11, Nov. 2013, pp. 2948-2956.

Betancourt et al. "Predicting Downhole Fluid Analysis Logs to Investigate Reservoir Connectivity," IPTC 11488, presented at International Petroleum Technology Conference, Dubai, U.A.E., Dec. 4-6, 2007, pp. 1-11.

Mullins et al. "Asphaltene Gravitational Gradient in a Deepwater Reservoir as Determined by Downhole Fluid Analysis", SPE 106375, 2007 SPE International Symposium on Oilfield Chemistry, Houston, Texas, Feb. 28-Mar. 2, 2007, pp. 1-6.

* cited by examiner

PREDICTION OF ASPHALTENE ONSET PRESSURE GRADIENTS DOWNHOLE

BACKGROUND

Wells are generally drilled into subsurface rocks to access fluids, such as hydrocarbons, stored in subterranean formations. The formations penetrated by a well can be evaluated for various purposes, including for identifying hydrocarbon reservoirs within the formations. Flow connectivity of a reservoir is one parameter that impacts the hydrocarbon production efficiency. Asphaltenes are generally the heaviest fraction and the most polar component in a petroleum mixture. They can be precipitated as solid particles under certain pressure and temperature conditions in some crude oils. As reservoir pressure decreases, the pressure (at a given test temperature) at which asphaltene precipitation begins is referred to as the asphaltene onset pressure (AOP).

Formation evaluation may involve drawing fluid from a formation into a downhole tool. In some instances, downhole fluid analysis (DFA) is used to test the fluid while it remains in the well. Such analysis can be used to provide information on certain fluid properties in real time without the delay associated with returning fluid samples to the surface. Information obtained through downhole fluid analysis can be used as inputs to various modeling and simulation techniques to estimate the properties or behavior of petroleum fluid in a reservoir. These techniques can employ an equation of state (EOS) model that represents the phase behavior of the petroleum fluid within the reservoir, which can be used to determine various other fluid or reservoir characteristics.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present disclosure, a method includes performing downhole fluid analysis of formation fluid via a downhole tool at a measurement station at a first depth in a wellbore. The method also includes determining an asphaltene gradient for the formation fluid at the measurement station. Further, the method includes predicting asphaltene onset pressure for a second depth in the wellbore based on results of the downhole fluid analysis and the determined asphaltene gradient.

In another embodiment, a method includes obtaining characteristics of samples of live oil drawn from a formation at multiple depths within a wellbore through downhole fluid analysis and determining asphaltene gradients for the samples. Additionally, the method includes predicting asphaltene instability for additional depths within the wellbore based on the obtained characteristics and the determined asphaltene gradients.

In a further embodiment, an apparatus includes a downhole sampling tool and a controller. The downhole sampling tool includes a downhole fluid analysis module for determining parameters of sampled fluids. Further, the controller can be used to predict asphaltene onset pressure at a depth in a well based on parameters determined by downhole fluid analysis for a fluid sampled from a formation by the downhole sampling tool at another depth in the well.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

The present disclosure relates to determining asphaltene instability or asphaltene onset pressure in hydrocarbon reservoirs. More particularly, in some embodiments asphaltene onset pressure is predicted by integrating DFA measurements and asphaltene concentration gradients analyses using the Flory-Huggins-Zuo equation of state model (FHZ EOS) in real time. The determined asphaltene onset pressure can also be used to analyze reservoir connectivity, asphaltene phase instability, and tar mat formation in oil columns.

As noted above and discussed more fully below, fluid characteristics determined by downhole fluid analysis can be used in predicting asphaltene onset pressures in hydrocarbon reservoirs. Such downhole fluid analysis can be performed with downhole tools of various wellsite systems, such as drilling systems and wireline systems. Embodiments of two such systems are depicted in FIGS. 1 and 2 by way of example.

Figure 1:
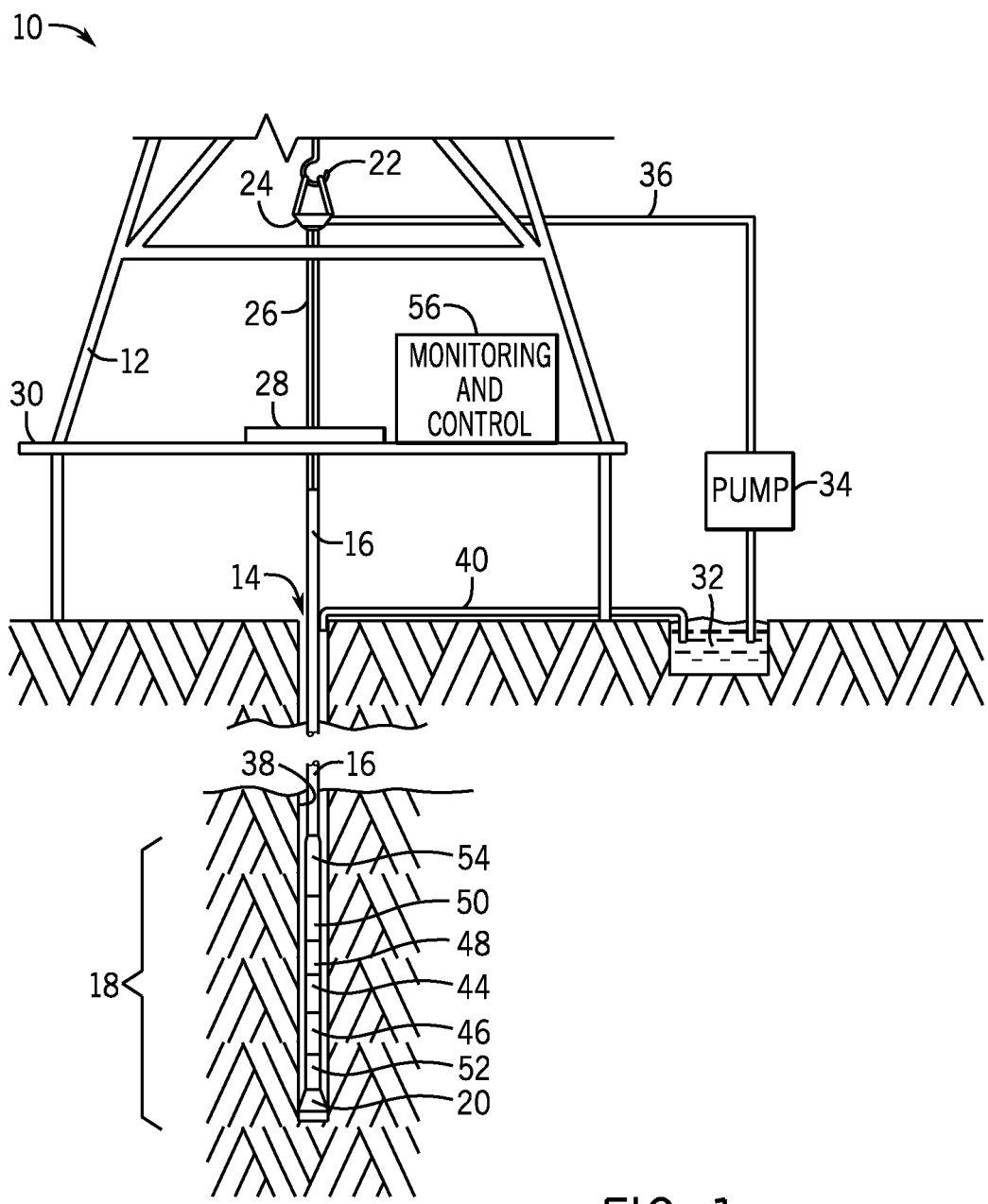
FIG. 1 generally depicts a drilling system having a fluid sampling tool in a drill string in accordance with one embodiment of the present disclosure.
Figure 2:
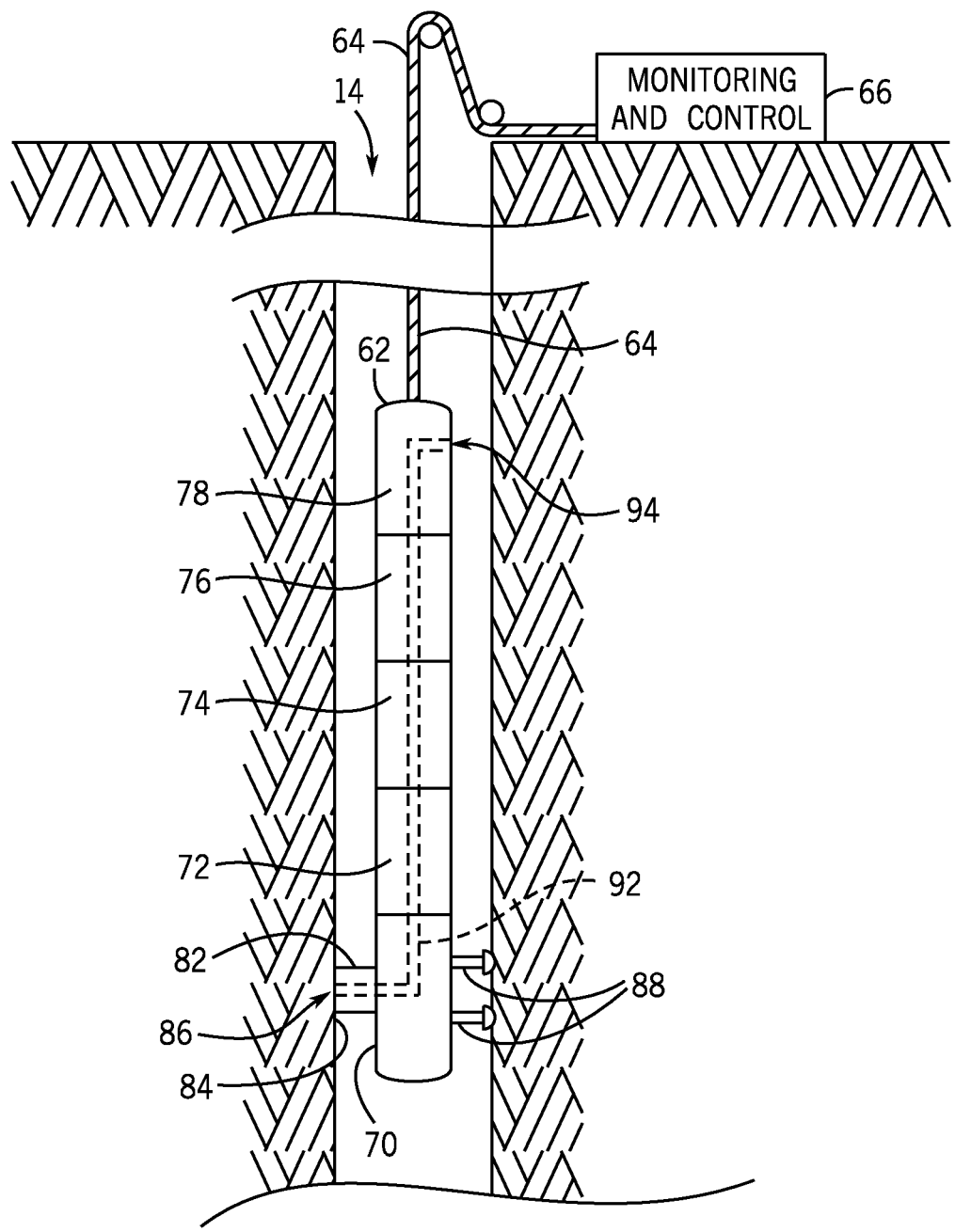
FIG. 2 generally depicts a fluid sampling tool deployed within a well on a wireline in accordance with one embodiment.

More specifically, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 includes a drilling rig 12 positioned over a well 14. Although depicted as an onshore drilling system 10, it is noted that the drilling system could instead be an offshore drilling system. The drilling rig 12 supports a drill string 16 that includes a bottomhole assembly 18 having a drill bit 20. The drilling rig 12 can rotate the drill string 16 (and its drill bit 20) to drill the well 14.

The drill string 16 is suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In the presently illustrated embodiment, a rotary table 28 on a drill floor 30 of the drilling rig 12 is constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 is circulated through the well 14 by a pump 34. The drilling fluid 32 is pumped from a mud pit (or some other reservoir, such as a mud tank) into the drill string 16 through a supply conduit 36, the swivel 24, and the kelly 26. The drilling fluid 32 exits near the bottom of the drill string 16 (e.g., at the drill bit 20) and returns to the surface through the annulus 38 between the wellbore and the drill string 16. A return conduit 40 transmits the returning drilling fluid 32 away from the well 14. In some embodiments, the returning drilling fluid 32 is cleansed (e.g., via one or more shale shakers, desanders, or desilters) and reused in the well 14.

In addition to the drill bit 20, the bottomhole assembly 18 also includes various instruments that measure information of interest within the well 14. For example, as depicted in FIG. 1, the bottomhole assembly 18 includes a logging-while-drilling (LWD) module 44 and a measurement-while-drilling (MWD) module 46. Both modules include sensors, housed in drill collars, that collect data and enable the creation of measurement logs in real-time during a drilling operation. The modules could also include memory devices for storing the measured data. The LWD module 44 includes sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in greater detail below, one or more of the modules 44, 46, and 48 is or includes a fluid sampling tool configured to obtain a sample of a fluid from a subterranean formation and perform downhole fluid analysis to measure various properties of the sampled fluid, which can then be used to predict asphaltene onset pressure.

The bottomhole assembly 18 can also include other modules. As depicted in FIG. 1 by way of example, such other modules include a power module 50, a steering module 52, and a communication module 54. In one embodiment, the power module 50 includes a generator (such as a turbine) driven by flow of drilling mud through the drill string 16. In other embodiments the power module 50 could also or instead include other forms of power storage or generation, such as batteries or fuel cells. The steering module 52 may include a rotary-steerable system that facilitates directional drilling of the well 14. The communication module 54 enables communication of data (e.g., data collected by the LWD module 44 and the MWD module 46) between the bottomhole assembly 18 and the surface. In one embodiment, the communication module 54 communicates via mud pulse telemetry, in which the communication module 54 uses the drilling fluid 32 in the drill string as a propagation medium for a pressure wave encoding the data to be transmitted.

The drilling system 10 also includes a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Another example of using a downhole tool for formation testing within the well 14 is depicted in FIG. 2. In this embodiment, a fluid sampling tool 62 is suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 controls movement of the fluid sampling tool 62 within the well 14 and receives data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) is incorporated into or as one or more modules of the bottom-hole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 includes a probe 82 that may be extended (e.g., hydraulically driven) and pressed into engagement against a wall 84 of the well 14 to draw fluid from a formation into the fluid sampling tool 62 through an intake 86. As depicted, the probe module 70 also includes one or more setting pistons 88 that may be extended outwardly to engage the wall 84 and push the end face of the probe 82 against another portion of the wall 84. In some embodiments, the probe 82 includes a sealing element or packer that isolates the intake 86 from the rest of the wellbore. In other embodiments the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 draws the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72, which may also be referred to as the fluid analyzer 72, includes one or more sensors for measuring properties of the sampled formation fluid, such as the optical density of the fluid, and the power module 76 provides power to electronic components of the fluid sampling tool 62.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Figure 3:
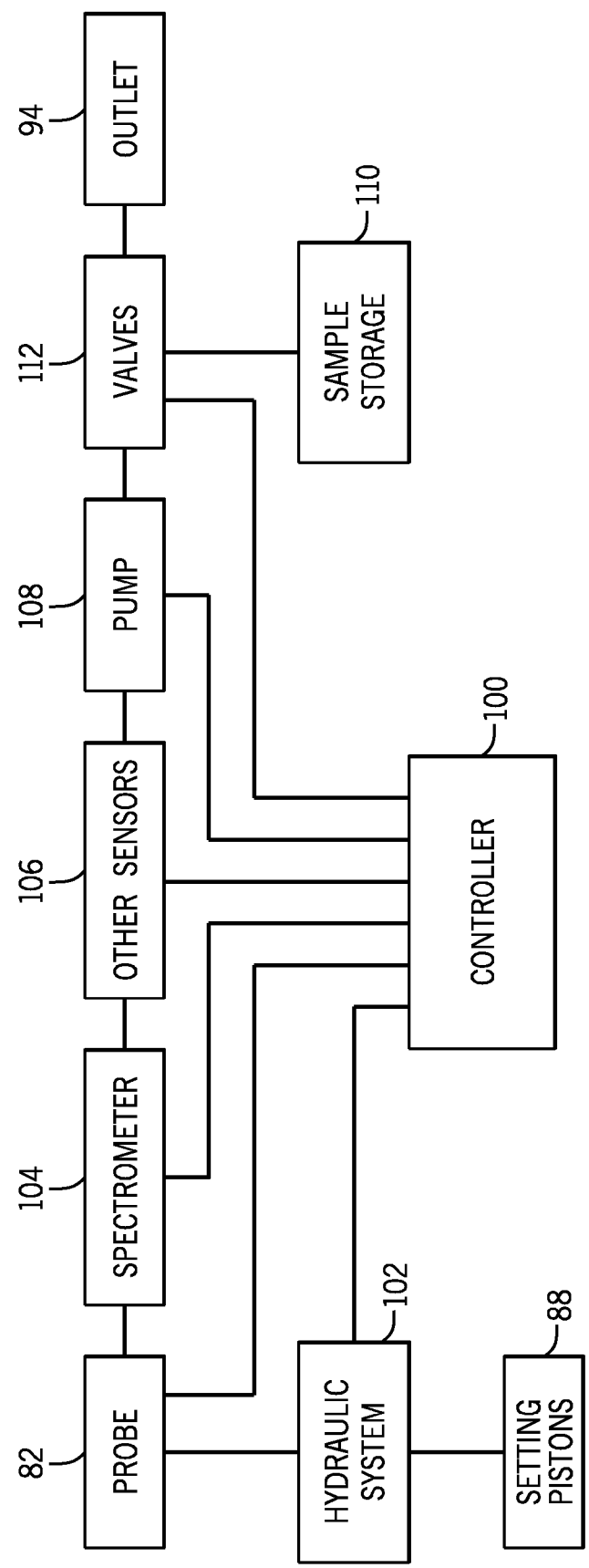
FIG. 3 is a block diagram of components of a fluid sampling tool operated by a controller in accordance with one embodiment.

Additional details as to the construction and operation of the fluid sampling tool 62 may be better understood through reference to FIG. 3. As shown in this figure, various components for carrying out functions of the fluid sampling tool 62 are connected to a controller 100. The various components include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94.

In operation, the hydraulic system 102 extends the probe 82 and the setting pistons 88 to facilitate sampling of a formation fluid through the wall 84 of the well 14. It also retracts the probe 82 and the setting pistons 88 to facilitate subsequent movement of the fluid sampling tool 62 within the well. The spectrometer 104, which can be positioned within the fluid analyzer 72, collects data about optical properties of the sampled formation fluid. Such measured optical properties can include optical densities (absorbance) of the sampled formation fluid at different wavelengths of electromagnetic radiation. Using the optical densities, the composition of a sampled fluid (e.g., volume fractions of its constituent components) can be determined. Other sensors 106 can be provided in the fluid sampling tool 62 (e.g., as part of the probe module 70 or the fluid analyzer 72) to take additional measurements related to the sampled fluid. In various embodiments, these additional measurements could include reservoir pressure ($P_{res}$) and temperature (T), live fluid density ($\rho$), live fluid viscosity ($\mu$), electrical resistivity, saturation pressure, and fluorescence, to name several examples. Other characteristics, such as gas-to-oil ratio (GOR) and asphaltene precipitation, can also be determined using the DFA measurements.

Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 facilitates operation of the fluid sampling tool 62 by controlling various components. Specifically, the controller 100 directs operation (e.g., by sending command signals) of the hydraulic system 102 to extend and retract the probe 82 and the setting pistons 88 and of the pump 108 to draw formation fluid samples into and through the fluid sampling tool. The controller 100 also receives data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 also operates the valves 112 to divert sampled fluids from the flowline 92 into the storage devices 110.

Figure 4:
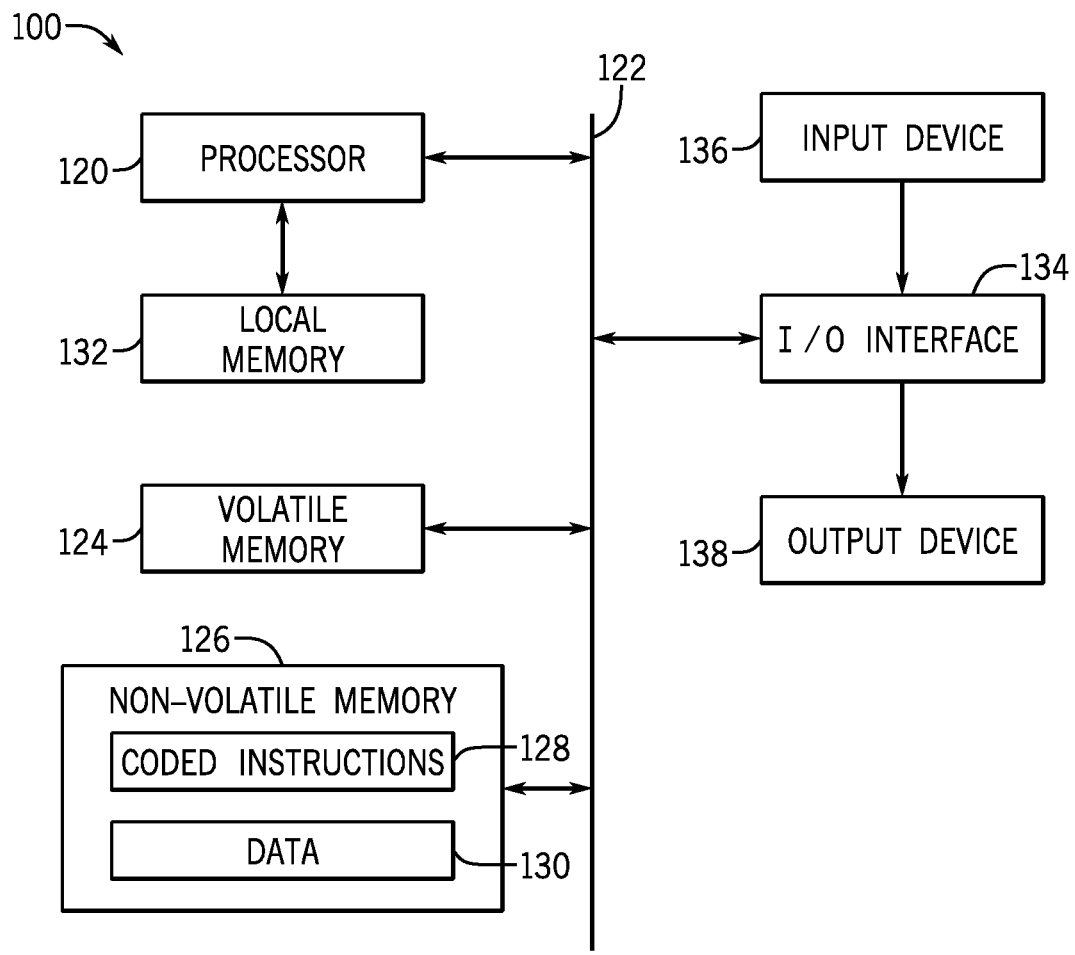
FIG. 4 is a block diagram of components in one example of the controller illustrated in FIG. 3.

The controller 100 in some embodiments is a processor-based system, an example of which is provided in FIG. 4. In this depicted embodiment, the controller 100 includes at least one processor 120 connected, by a bus 122, to volatile memory 124 (e.g., random-access memory) and non-volatile memory 126 (e.g., flash memory and a read-only memory (ROM)). Coded application instructions 128 (e.g., software that may be executed by the processor 120 to enable the control and analysis functionality described herein, including AOP prediction and reservoir evaluation) and data 130 are stored in the non-volatile memory 126. For example, the application instructions 128 can be stored in a ROM and the data can be stored in a flash memory. The instructions 128 and the data 130 may be also be loaded into the volatile memory 124 (or in a local memory 132 of the processor) as desired, such as to reduce latency and increase operating efficiency of the controller 100.

An interface 134 of the controller 100 enables communication between the processor 120 and various input devices 136 and output devices 138. The interface 134 can include any suitable device that enables such communication, such as a modem or a serial port. In some embodiments, the input devices 136 include one or more sensing components of the fluid sampling tool 62 (e.g., the spectrometer 104) and the output devices 138 include displays, printers, and storage devices that allow output of data received or generated by the controller 100. Input devices 136 and output devices 138 may be provided as part of the controller 100, although in other embodiments such devices may be separately provided.

The controller 100 can be provided as part of the monitoring and control systems 56 or 66 outside of a well 14 to enable downhole fluid analysis of samples obtained by the fluid sampling tool 62. In such embodiments, data collected by the fluid sampling tool 62 can be transmitted from the well 14 to the surface for analysis by the controller 100. In some other embodiments, the controller 100 is instead provided within a downhole tool in the well 14, such as within the fluid sampling tool 62 or in another component of the bottomhole assembly 18, to enable downhole fluid analysis to be performed within the well 14. Further, the controller 100 may be a distributed system with some components located in a downhole tool and others provided elsewhere (e.g., at the surface of the wellsite). Whether provided within or outside the well 14, the controller 100 can receive data collected by the sensors within the fluid sampling tool 62 and process this data to determine one or more characteristics of interest for the sampled fluid.

In accordance with the present disclosure, the systems described above can be used to predict asphaltene onset pressure over a range of formation depths based on downhole fluid analysis of formation fluid samples. In some embodiments, the Flory-Huggins-Zuo EOS model is used to identify asphaltene instability (asphaltene onset pressure prediction) along the reservoir depth. Using this model and downhole fluid analysis measurements, fluid phase information, such as the asphaltene onset pressure at different depths, can be predicted qualitatively and quantitatively downhole in real time.

Figure 5:
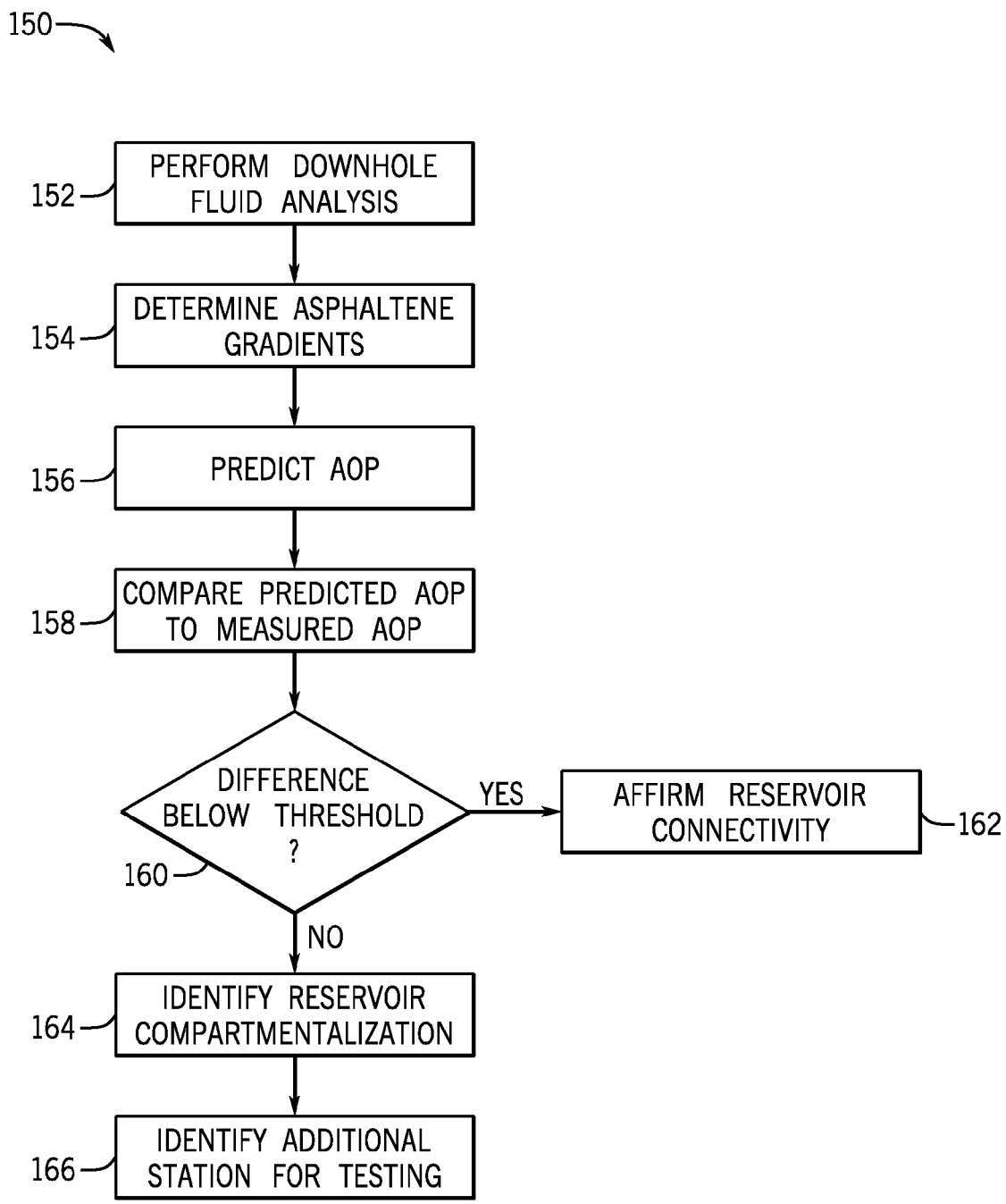
FIG. 5 is a flow chart for predicting asphaltene onset pressure and evaluating a reservoir in accordance with one embodiment.

By way of example, one embodiment of a process for predicting asphaltene onset pressures is generally represented by flow chart 150 in FIG. 5. In this embodiment, downhole fluid analysis is performed on formation fluids (block 152). For instance, a fluid sampling tool of either the drilling system or wireline system described above with respect to FIGS. 1 and 2 (e.g., fluid sampling tool 62) can be used to sample reservoir fluid at one or more measurement stations within a wellbore (e.g., the well 14) and analyze the sampled fluids downhole (e.g., at each measurement station). More specifically, a formation fluid can be drawn into the fluid sampling tool and analyzed while the tool is positioned at a first depth (or station) within the well to determine a first set of formation fluid characteristics. The tool may then be moved successively to additional stations at different depths to sample and analyze fluids at each station. Such downhole fluid analysis enables in situ determinations of numerous characteristics of the sampled fluids in real time, including density, viscosity, saturation pressure, reservoir pressure, reservoir temperature, temperature gradient, GOR, oil-based mud (OBM) contamination, optical density, mass composition, asphaltene onset pressure, and true vertical depth (of the measurement station at which the fluid was sampled).

Results of the downhole fluid analysis can be used to determine asphaltene gradients at the measurement stations (block 154). These asphaltene gradients can be determined through any suitable technique. In at least some embodiments the asphaltene gradients in the reservoir are determined through the use of the Flory-Huggins-Zuo EOS (FHZ EOS) model. The FHZ EOS model employs an equation of state together with flash calculations to predict compositions (including asphaltene) as a function of depth in the reservoir. The equation of state represents the phase behavior of the compositional components of the reservoir fluid. Such equation of state can take many forms, such as any one of many known cubic EOS. The equation of state is extended to predict compositional gradients (including an asphaltene compositional gradient) with depth that take into account the impacts of gravitational forces, chemical forces, and thermal diffusion. The flash calculations solve for fugacities of components that form at equilibrium. The asphaltene compositional gradient produced by the FHZ EOS model can be used to derive a profile of asphaltene pseudocomponents (e.g., asphaltene nanoaggregates and larger asphaltene clusters) and corresponding aggregate size of asphaltenes as a function of depth in the reservoir of interest.

The FHZ EOS model governing asphaltene grading is given by:

$$\frac{OD(h_2)}{OD(h_1)} = \frac{\phi_a(h_2)}{\phi_a(h_1)} = \exp\left(\frac{v_a g(\rho - \rho_a)(h_2 - h_1)}{RT} + \left(\frac{v_a}{v}\right)_{h_2} - \left(\frac{v_a}{v}\right)_{h_1} - \frac{v_a\left[(\delta_a - \delta)_{h_2}^2 - (\delta_a - \delta)_{h_1}^2\right]}{RT}\right) \quad (1)$$

where $\phi_a(h_1)$ is the volume fraction for the asphaltene component of an oil mixture at depth $h_1$; $\phi_a(h_2)$ is the volume fraction for the asphaltene component at depth $h_2$; $v_a$ is the molar volume for the asphaltene component; v is the molar volume for the oil mixture; $\delta_a$ is the solubility parameter for the asphaltene component; $\delta$ is the solubility parameter for the oil mixture; $\rho_a$ is the density for the asphaltene component; $\rho$ is the density for the oil mixture; R is the universal gas constant; g is the gravitational constant; T is the absolute temperature of the reservoir fluid; $OD(h_1)$ is the optical density (coloration) at depth $h_1$; and $OD(h_2)$ is the optical density at depth $h_2$.

The first term in the exponential of Equation (1) is the gravity contribution, which depends on the difference in densities between the asphaltenes and the bulk oil. The second and third terms in the exponential are the combinatorial entropy contribution, which depend on the change in volume of the bulk oil with respect to depth, accounting for the entropy of mixing. The final term in the exponential is the enthalpy (solubility) contribution that depends on the difference between the solubility parameters of the asphaltenes and the bulk oil. Equation (1) can be solved numerically to obtain asphaltene grading.

Most of the parameters of the FHZ EOS model are either constants or can be obtained via the downhole fluid analysis described above and cubic equations of state. If oil properties and the asphaltene solubility parameter at different depths are obtained, the single adjustable parameter is the size (e.g., molar volume or diameter) of asphaltenes, which is determined by matching the optical density measured by downhole fluid analysis. In some embodiments, this parameter can be tuned by comparing the obtained size with the Yen-Mullins model to check for consistency. Generally, the size of asphaltenes can be assumed to be one of three asphaltene forms in the Yen-Mullins model (asphaltene molecules at low concentrations, nanoaggregates at medium concentrations, or clusters of nanoaggregates at high concentrations). The asphaltene gradients can then be determined (e.g., predicted) by the FHZ EOS model.

If the oil properties change with depth, the cubic EOS is used to describe such equilibrium or non-equilibrium phase behavior of the reservoir fluid. Therefore, the oil properties at different depths are calculated by using the cubic EOS. Subsequently, the FHZ EOS is used to calculate local asphaltene equilibration with a local fluid at each small vertical depth interval. Thus, the asphaltene gradient in the equilibrium or non-equilibrium hydrocarbon reservoir column can be obtained, which can be subsequently used for reservoir connectivity analysis.

Asphaltene onset pressure for a range of reservoir depths may then be predicted (block 156) based on the results of the downhole fluid analysis and the determined asphaltene gradients. By way of example, once asphaltene gradients (asphaltene concentration or fluid composition at different depth) are obtained, phase equilibrium (such as P-T flash) calculations can be performed at each of the set of depths. To conduct this calculation, the following equilibrium criteria should be satisfied for the components at each depth $$x_i^{oil}\gamma_i^{oil} = x_i^{asph}\gamma_i^{asph} \quad (2)$$

where superscripts oil and asph represent the oil and asphaltene phases, x is the mole fraction, and γ is the activity coefficient. Because the equilibrium criteria are used at the same depth for both phases, the gravitational term can be canceled out in the FHZ EOS model and the Flory-Huggins regular solution model can be used in the asphaltene instability analysis.

Prior to the phase equilibrium calculation, a phase stability test can be performed to check whether the crude oil is stable in a single-phase state without asphaltene separation (i.e., whether the asphaltenes can be stably dispersed or suspended in crude oils). Generally, the system is stable if the Gibbs free energy of the system reaches the minimum. Hence, the single phase stability testing is performed based on the reduced molar Gibbs tangent plane distance (TPD) function:

$$TPD(\{y_i^{trial}\}) = \quad (3)$$

$$\sum_{i=1}^{C} y_i^{trial}[\ln \phi_i(\{y_i^{trial}\}) + \ln y_i^{trial} - \ln \phi_i(\{z_i^{test}\}) - \ln z_i^{test}]$$

where $\{y_i^{trial}\}$ and $\{z_i^{test}\}$ are the compositions of the trial and test phases, respectively; and $\phi_i(\{y_i^{trial}\})$ and $\phi_i(\{z_i^{test}\})$ are the fugacity coefficients of component i in the trial and test phases, respectively. If the minimum value of the TPD function is negative, the test phase is not stable. In other words, asphaltene instability occurs if more than one phase exists. Generally, in a liquid system, the fugacity coefficients of components i (either maltenes or asphaltenes) is calculated by the activity coefficients as follows:

$$\ln \gamma_i^\alpha = \ln\left(\frac{v_i^\alpha}{v^\alpha}\right) + 1 - \frac{v_i^\alpha}{v^\alpha} + \frac{v_i^\alpha}{RT}(\delta_i - \delta)^2 \quad (4)$$

where superscript α denotes phase oil or asph. The mixture v and δ are calculated by:

$$v = \sum_i x_i v_i \quad (5)$$

$$\delta = \sum_i \phi_i \delta_i \quad (6)$$

The phase equilibrium calculations noted above can be performed after the phase stability check based on the gradients calculated by the FHZ EOS model at specified depth, temperature and pressure. Notably, in some embodiments the parameters used in asphaltene gradients analysis and asphaltene instability analysis are the same, enabling a single model to work for both asphaltene grading and phase transition predictions.

Bulk fluid properties may be used to apply the FHZ EOS model for asphaltene gradients and asphaltene phase instability analyses. An equation of state approach (e.g., using the cubic EOS) can be used to calculate compositional grading without taking into consideration asphaltenes separately and specially. Fluid properties, such as component and bulk partial molar volume, compositions, density, molecular weight, and the like, can be calculated by the equation of state. Because the equation of state is typically tuned to match pressure-volume-temperature (PVT) properties of the fluids in question to obtain the fluid model, the properties calculated by the equation of state are bulk fluid properties, including the resin and asphaltene contributions. Therefore, the mixing rules of v, ρ, and δ may not be used for oil because the values estimated in this way represent bulk (maltene plus asphaltene) v, ρ, and δ On the other hand, once fluid properties of the mixture are obtained, properties of maltenes can be obtained by use of the mixing rules.

The solubility parameters can be calculated by use of either the equation of state or correlations. In one embodiment, the solubility parameter of asphaltene used in the gradients analysis is initially described by an empirical correlation. Then the value of the solubility parameter of asphaltene can be tuned (based on additional information) to match asphaltene onset pressure measured in the asphaltene instability analysis using the Flory-Huggins regular solution model. It will be further appreciated that the measurements obtained through downhole fluid analysis can be used to tune the FHZ EOS model. Such tuning can increase the accuracy of future predictions of reservoir fluid properties, and modeling via the FHZ EOS model could be repeated as desired for additional predictions of reservoir fluid properties.

Figure 6:
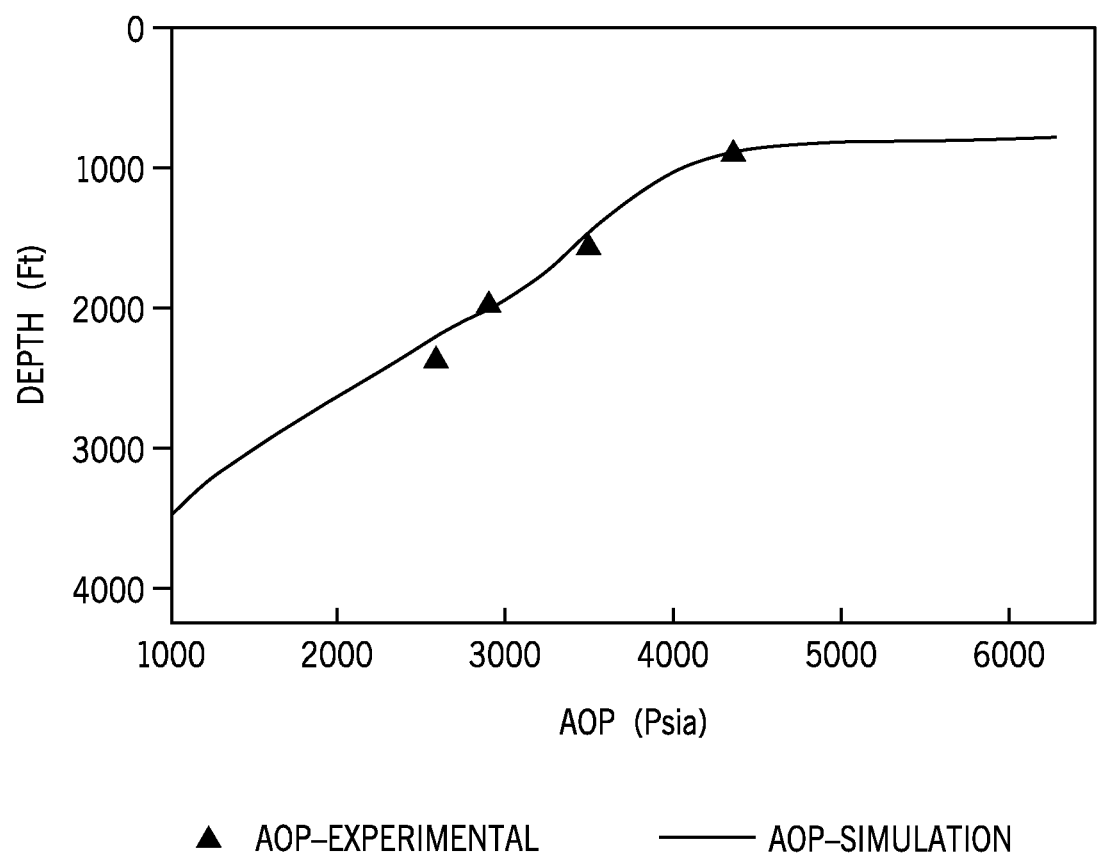
FIG. 6 is a graph showing results of a prediction of asphaltene onset pressure over a range of depths in accordance with one embodiment.

Once parameter estimation completed, the asphaltene onset pressure at different depths can be predicted using a simulator. One example of predicted asphaltene onset pressure at different depths is depicted in FIG. 6. In this figure, the predicted asphaltene onset pressure (represented by the solid curve) is shown as varying with depth. Asphaltene onset pressures measured at four different depths are also plotted on the graph of FIG. 6.

As described above, the FHZ EOS model is used to calculate asphaltene gradients and compare the obtained asphaltene size with the Yen-Mullins model to check for size consistency between the models. The predicted asphaltene onset pressure at each depth can be checked by solving Equations (2)-(4) to see whether they are stable or not. If they are not stable and have asphaltene nanoaggregates or clusters, a tar mat (generally a discontinuity in asphaltene content with depth) may form. In this case, various techniques could be used to provide additional insight into the discontinuity. For instance, core samples could be collected at locations where asphaltene might be destabilized to determine whether solid asphaltenes are in the core samples or oil samples could be collected for geochemistry analysis to determine if a late stage of gas charging occurred in the reservoir. Further, as a data consistency technique, if an asphaltene onset pressure is not available downhole, collected oil samples could be checked for asphaltene onset pressure to test whether the believed discontinuity is, in fact, accurate (rather than being the result of a measurement or some other error). Also, through comparison of the predicted and measured asphaltene onset pressures, a flow assurance problem can be identified, and a comprehensive flow assurance study can be performed in a laboratory for additional information. Still further, if the data implies a large viscosity increase, lab analysis or other downhole measurements can be conducted to confirm that implication.

If samples are stable and have asphaltene clusters, then heavy oil or bitumen (continuity in asphaltene content with depth) is indicated. A continuous bitumen layer (another kind of tar mat) may form at the base in such cases. This implies large asphaltene gradients, as well as large increases in viscosity and specific gravity (e.g., American Petroleum Institute (API) gravity). Because of an exponential increase in asphaltene content with depth, asphaltene viscosity increases exponentially to large values. In such cases, the asphaltene movement may be limited and they may form a bitumen layer that inhibits flow through a formation matrix.

The predicted asphaltene onset pressure gradient can be used for a variety of purposes, such as reservoir characterization. For example, in certain embodiments, a comparison of the measured and predicted asphaltene onset pressures can be effected (block 158). In the embodiment represented in FIG. 5, the predicted asphaltene onset pressure can be used to evaluate reservoir connectivity. Particularly, the magnitude of the difference between the measured and predicted asphaltene onset pressures can be compared to a threshold to determine (block 160) whether a reservoir is connected between two depths or is compartmentalized. For instance, based on known fluid parameters and asphaltene gradients determined at one or more depths in the well, an asphaltene onset pressure prediction can be made at an additional depth. The prediction can be based on an assumption of connectivity between the one or more depths and the additional depth. If the magnitude of the difference between the predicted and measured asphaltene onset pressures for the additional depth is small (e.g., below the threshold), the difference can likely be attributed to uncertainty in the prediction or measurement and connectivity of the reservoir between the one or more depths and the additional depth can be affirmed (block 162). Conversely, compartmentalization can be identified (block 164) from large differences (e.g., above the threshold magnitude) between the predicted and measured asphaltene onset pressures for the additional depth. In this case, one or more additional stations in the wellbore can be identified (block 166) for additional downhole fluid analysis. At these additional stations (e.g., between two stations indicated as compartmentalized), downhole fluid analysis can be performed and the asphaltene gradient can be determined as described above. Such additional data can be used to determine the source of the previous discrepancy between the measured and predicted asphaltene onset pressure measurements.

Various processes disclosed herein, including that generally represented by flow chart 150, can be carried out by any suitable devices or systems, such as the controller 100 in connection with a downhole tool (e.g., LWD module 44 or additional module 48 of FIG. 1, or fluid sampling tool 62 of FIG. 2). These suitable devices and systems can use algorithms, executable code, lookup tables, and the like to carry out the functionality described above. Also, in some embodiments these processes may be performed in substantially real time without removing fluid samples from the well 14.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method comprising:
performing downhole fluid analysis of formation fluid via a downhole tool at a measurement station at a first depth in a wellbore;
determining an asphaltene gradient for the formation fluid at the measurement station; and
predicting asphaltene onset pressure for a second depth in the wellbore based on results of the downhole fluid analysis and the determined asphaltene gradient, wherein asphaltene onset pressure corresponds to a pressure at which asphaltene precipitation begins.

2. The method of claim 1, comprising evaluating reservoir connectivity based on the predicted asphaltene onset pressure for the second depth.

3. The method of claim 2, wherein evaluating reservoir connectivity includes comparing the predicted asphaltene onset pressure for the second depth with a measured asphaltene onset pressure that is measured at the second depth.

4. The method of claim 3, wherein evaluating reservoir connectivity includes determining whether the magnitude of the difference between the measured asphaltene onset pressure at the second depth and the predicted asphaltene onset pressure for the second depth is below a threshold.

5. The method of claim 4, comprising affirming reservoir connectivity based on a determination that the magnitude of the difference between the measured asphaltene onset pressure at the second depth and the predicted asphaltene onset pressure for the second depth is below the threshold.

6. The method of claim 4, comprising identifying reservoir compartmentalization based on a determination that the magnitude of the difference between the measured asphaltene onset pressure at the second depth and the predicted asphaltene onset pressure for the second depth is above the threshold.

7. The method of claim 6, comprising identifying, based on the identification of reservoir compartmentalization, an additional station in the wellbore at which to perform downhole fluid analysis of formation fluid via the downhole tool and determine an asphaltene gradient for the formation fluid.

8. The method of claim 7, comprising:
performing downhole fluid analysis of formation fluid via the downhole tool at the additional station; and
determining the asphaltene gradient for the formation fluid at the additional station.

9. The method of claim 1, comprising using the Flory-Huggins-Zuo equation of state model in determining the asphaltene gradient for the formation fluid at the measurement station.

10. The method of claim 9, comprising using a cubic equation of state with the Flory-Huggins-Zuo equation of state model in determining the asphaltene gradient for the formation fluid at the measurement station.

11. The method of claim 1, comprising identifying a flow assurance problem based on the predicted asphaltene onset pressure for the second depth and an asphaltene onset pressure measured at the second depth.

12. A method comprising:
obtaining characteristics of samples of live oil drawn from a formation at multiple depths within a wellbore through downhole fluid analysis;
determining asphaltene gradients for the samples; and
predicting asphaltene instability for additional depths within the wellbore based on the obtained characteristics and the determined asphaltene gradients, wherein predicting asphaltene instability comprises predicting asphaltene onset pressures for the additional depths, and asphaltene onset pressure corresponds to a pressure at which asphaltene precipitation begins.

13. The method of claim 12, wherein predicting asphaltene instability includes performing phase equilibrium calculations at the multiple depths.

14. The method of claim 13, comprising verifying that the live oil is stable in a single-phase state without asphaltene separation before performing the phase equilibrium calculations.

15. The method of claim 12, wherein predicting asphaltene instability includes analyzing asphaltene instability using the Flory-Huggins regular solution model.

16. The method of claim 12, comprising determining the sizes of asphaltenes of the samples and checking the determined sizes for consistency with the Yen-Mullins model.

17. An apparatus comprising:
a downhole sampling tool including a downhole fluid analysis module configured to determine parameters of sampled fluids; and
a controller operable to predict asphaltene onset pressure at a depth in a well based on parameters determined by downhole fluid analysis for a fluid sampled from a formation by the downhole sampling tool at another depth in the well, wherein asphaltene onset pressure corresponds to a pressure at which asphaltene precipitation begins.

18. The apparatus of claim 17, wherein the controller is operable to compare a predicted asphaltene onset pressure at the depth in the well to a measured asphaltene onset pressure at the depth and to characterize a reservoir based on the comparison.

19. The apparatus of claim 17, wherein the controller is operable to predict asphaltene onset pressure at the depth in the well based on parameters determined by downhole fluid analysis for the fluid sampled from the formation by the downhole sampling tool at another depth in the well and from an asphaltene gradient determined at the another depth.

20. The apparatus of claim 17, wherein at least a portion of the controller is provided within the downhole sampling tool.

* * * * *